United States Patent
Hasegawa (10) Patent No.: US 10,302,548 B2
(45) Date of Patent: May 28, 2019

(54) FLUORESCENT PARTICLE MEASURING METHOD

(71) Applicant: Azbil Corporation, Tokyo (JP)

(72) Inventor: Norio Hasegawa, Tokyo (JP)

(73) Assignee: Azbil Corporation, Tokyo (JP)

( * ) Notice: Subject to any disclaimer, the term of this patent is extended or adjusted under 35 U.S.C. 154(b) by 322 days.

(21) Appl. No.: 15/252,779

(22) Filed: Aug. 31, 2016

(65) Prior Publication Data

US 2017/0059470 A1 Mar. 2, 2017

(30) Foreign Application Priority Data

Sep. 2, 2015 (JP) ................................ 2015-173265

(51) Int. Cl.
  *G01N 21/64* (2006.01)
  *G01N 15/14* (2006.01)
  *G01N 15/00* (2006.01)

(52) U.S. Cl.
  CPC ..... *G01N 15/1456* (2013.01); *G01N 21/6458* (2013.01); *G01N 2015/0053* (2013.01); *G01N 2201/12* (2013.01)

(58) Field of Classification Search
  CPC ....... G01N 15/1456; G01N 2015/0053; G01N 21/6458; G01N 2201/12
  See application file for complete search history.

(56) References Cited

U.S. PATENT DOCUMENTS

2004/0136870 A1* 7/2004 Kochy ............... G01N 15/1456
422/73

FOREIGN PATENT DOCUMENTS

JP   H08-29331 A   2/1996
JP   2011-83214   4/2011

OTHER PUBLICATIONS

Hasegawa, Norio, et al., "Instantaneous Bioaerosol Detection Technology and Its Application", Yamatake Corporation, Azbil Technical Review, Dec. 2009, pp. 2-7, 2009.
Matsuki, Atsushi, "Atmospheric Aerosol Research Using Raman Microscopy", Aerosol Research, 2013, vol. 28, No. 3, pp. 208-213).

* cited by examiner

*Primary Examiner* — Mark R Gaworecki
(74) *Attorney, Agent, or Firm* — Oblon, McClelland, Maier & Neustadt, L.L.P.

(57) ABSTRACT

A fluorescent particle measuring method comprising the steps of trapping a fluorescent particle included in a fluid that is to be evaluated; identifying, by a material analyzing device, a material of a fluorescent particle that has been trapped; measuring, by a fluorescent particle measuring device, a number of fluorescent particles included in the fluid; and identifying, as the material of a fluorescent particle that has been measured by the fluorescent particle measuring device, a material identified by the material analyzing device.

12 Claims, 9 Drawing Sheets

| Number of Non-Fluorescent Particles (Particles/mL) | 5861 |
|---|---|
| Number of Fluorescent Particles (mL) | 340 |
| Total Number of Particles (mL) | 6201 |
| Proportion of Particles That Are Fluorescent (%) | 5.5 |

…

FLUORESCENT PARTICLE MEASURING METHOD

CROSS-REFERENCE TO RELATED APPLICATION

This application claims priority to Japanese Application No. 2015-173265 filed Sep. 2, 2015. This application is incorporated herein in its entirety.

TECHNICAL FIELD

The present disclosure relates to an environmental technology, and, in particular, to a fluorescent particle measuring method.

BACKGROUND

In a clean room, such as a bio clean room, airborne microorganism particles and non-microorganism particles are detected and recorded using a particle detecting device (referencing, for example, Japanese Unexamined Patent Application Publication No. 2011-83214 and N. Hasegawa, et al., "Real-time Detecting Technologies for Airborne Microbes, and Applications Thereof," Yamatake Corporation, Azbil Technical Review, December 2009, Pages 2-7, 2009). The state of wear of the air-conditioning equipment of the clean room can be ascertained from the result of the particle detection. Moreover, a record of particle detection within the clean room may be added as reference documentation to the products manufactured within the clean room. Optical particle detecting devices draw in air from a clean room, for example, and illuminate the drawn-in air with light. If a microorganism particle or non-microorganism particle is included in the air, then the particle that is illuminated by the light will produce fluorescence or scattered light will be produced by the particle. Because of this, it is possible to detect the numbers and sizes of microorganism particles and non-microorganism particles that are included in a gas, through detecting the fluorescent and scattered light. Moreover, a technology able to detect accurately particles in not just clean rooms, but in fluids as well, is desired (referencing, for example, Japanese Unexamined Patent Application Publication No. H8-29331). Moreover, there has been a proposal for identifying aerosol materials through Raman spectroscopy (referencing, for example, MATSUKI, Atsushi, "Atmospheric Aerosol Research Using Raman Microscopy," Aerosol Research, 2013, Vol. 28, No. 3, pp. 208-213).

SUMMARY

The wavelength band and strength of fluorescent light detected by the particle detecting device is correlated with the material of the fluorescent particle that emits the fluorescent light, but it is still difficult to identify accurately the material of the fluorescent particle from the wavelength band and strength of the fluorescent light alone. Given this, one object of the present disclosure is to provide a fluorescent particle measuring method able to identify accurately the material of fluorescent particles that are counted.

The present disclosure provides fluorescent particle measuring method including: (a) trapping a fluorescent particle included in a fluid that is to be evaluated; (b) identifying, by a material analyzing device, a material of a fluorescent particle that has been trapped; (c) measuring, by a fluorescent particle measuring device, a number of fluorescent particles included in the fluid; and (d) identifying, as the material of a fluorescent particle that has been measured by the fluorescent particle measuring device, a material identified by the material analyzing device.

In this method, the fluorescent particle included in the fluid that is subject to the evaluation may be trapped on a flat surface; the position of the fluorescent particle on the flat surface may be identified; and the material analyzing device may identify the material of the fluorescent particle at the position that has been identified. Moreover, the position of the fluorescent particle on the flat surface may be identified by the fluorescent light observing device.

In the method described above, the fluorescent light observing device may identify at least two reference points on the flat surface and may identify coordinates of a fluorescent particle relative to the at least two reference points.

In the method described above, the fluorescent light observing device may identify at least two reference points on the flat surface, may identify coordinates of the fluorescent particle relative to one of the at least two reference points, and, based on an angle formed between a line connecting the reference points and a coordinate axis of a sample stage of the fluorescent light observing device whereon an object that is provided with the flat surface is placed, may convert the coordinates of the fluorescent particle to identify coordinates of the fluorescent particle relative to the at least two reference points.

In the method described above, the material analyzing device may identify the reference points that have been identified by the fluorescent light observing device, and based on the angle formed between a line connecting the reference points and a coordinate axis of a sample stage of the material analyzing device on which is placed an object that is provided with the flat surface, may convert the coordinates of the fluorescent particle relative to the at least two reference points to identify coordinates of the fluorescent particle in the coordinate system of the sample stage of the material analyzing device.

In the method described above, the fluorescent light observing device may be a fluorescent microscope or a fluorescent imager. The material analyzing device may be a Raman spectroscope, an infrared spectroscope, or an electron beam microanalyzer.

In the method described above, an event wherein the fluorescent particle has been produced may be identified based on the identified material of the fluorescent particle. Moreover, in the method described above, the state of occurrence of an event may be monitored by the fluorescent particle measuring device based on the measurement result of the number of fluorescent particles.

In the method described above, the fluid may be a gas or a liquid.

The present disclosure enables the provision of a fluorescent particle measuring method able to identify accurately the material of fluorescent particles that are counted.

DETAILED DESCRIPTION

Examples of the present disclosure will be described below. Note that the descriptions and drawings that form a portion of the present disclosure should not be understood to be limiting the present disclosure. A variety of alternate technologies and application technologies should be clear, from the present disclosure, to a person skilled in the art, and it should be understood that the present disclosure includes a variety of examples, and the like, that are not described herein.

Figure 1:
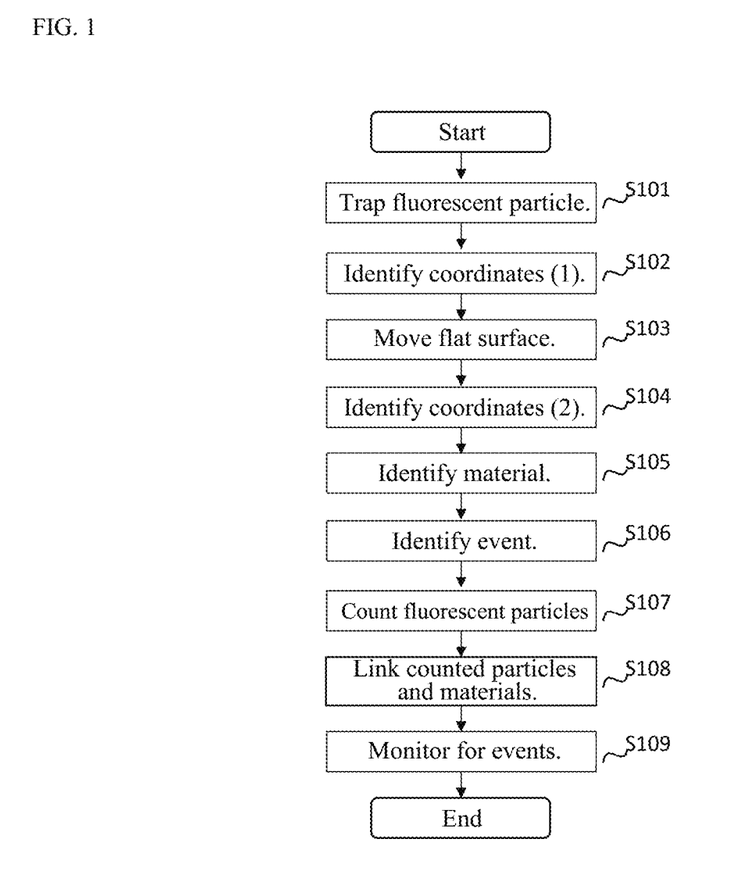
FIG. 1 is a flowchart of a fluorescent particle measuring method according to an example according to the present disclosure.

The fluorescent particle measuring method according to the present example, includes, as illustrated in FIG. 1, a Step S101 for trapping a fluorescent particle that is included in a fluid that is to be evaluated, a Step S105 for identifying, through a material analyzing device, the material of the trapped fluorescent particle; a Step S107 for measuring, through a fluorescent particle measuring device, the number of fluorescent particles included in the fluid, and a Step S108 wherein the material of the fluorescent particle measured by the fluorescent particle measuring device is recognized as the material identified by the material analyzing device.

The "fluid" may be a gas or a liquid. Examples of gases include outdoor gases and indoor gases, but there is no limitation thereto. Examples of liquids include purified water, water for pharmaceutical manufacturing, water for infusions, environmental water, and liquid reagents, but there is no limitation thereto. The fluorescent particles include organism particles and non-organism particles. Note that "fluorescence" includes auto-fluorescence.

When the fluorescent particle is an organism particle, such as a microorganism, the nicotinamide adenine dinucleotides and riboflavin, and the like, within the microorganisms produce florescent light. Pollen also produces fluorescent light. Even when the non-biologic particles are illuminated with light, the non-biologic particle may emit light in the fluorescent band. Fluorescent particles that fall off of a polyester gown, for example, that has been cleaned will emit fluorescence when illuminated with light. Polystyrene particles also emit fluorescence, and then fade.

When the fluid that is subject to evaluation is purified water, in some cases non-microorganism particles comprising the materials of the purified water manufacturing device may be included in the purified water. For example, particles made from materials that are one or more selections from polypropylene, polyethylene, polytetrafluoroethylene (PTFE), olefin, polycarbonate, polyurethane, and the like, may be produced from the filter or housing of the purified water manufacturing device. Particles made from materials that are one or more selections from, for example, silicon rubber, nitrile rubber (NBR), ethylenepropylene rubber (EPDM), fluorine rubber, kalrez, PTFE, and the like, may be produced by the packing that is provided in the purified water manufacturing device. Particles made from one or more selections from Viton, fluorine resins, silicon resins, polyamide, polyphenylene sulfide (PPS), perfluoro, and the like, may be produced from the pump that is provided in the purified water manufacturing device. Particles of PTFE, or the like, may be produced from the seals that are installed in the purified water manufacturing device. Particles made from metal materials, such as oxidized stainless steel, or the like, may be produced from the pipes in the purified water manufacturing device. When the materials of the particles that may be produced from the purified water manufacturing device, as described above, are exposed to an excitation beam, in some cases they will produce florescent light or light having a wavelength band that overlaps that of fluorescent light.

In Step S101, a fluorescent particle that is included in the fluid that is subject to evaluation, and for which the material has not yet been identified, is trapped on, for example, a flat surface. The flat surface may be, for example, a membrane in a filter, or the like, a glass substrate, a resin substrate, a metal substrate, or the like. The flat surface has, for example, a rectangular shape. An object that has a rectangular flat surface may be cut out of an object that has a flat surface of another shape.

A fluorescent particle that is included in the fluid is trapped on a flat surface when, for example, the fluid passes through a membrane. Conversely, the method for trapping the fluorescent particles may be, for example, one wherein the fluorescent particles are electrostatically directed onto the flat surface, one wherein the fluorescent particles are caused through inertia to collide with the flat surface, one wherein the fluorescent particles are caused to move to the flat surface through dielectricphoresis, one wherein fluorescent particles are separated from a fluid and directed onto the flat surface through a cyclone vacuum device, one wherein Coriolis forces are used to separate the fluorescent particles from the fluid and direct them to the flat surface, or the like.

After Step S101, in Step S102, the coordinates of fluorescent particles on the flat surface are identified. For example, an object such as a membrane or substrate that is provided with a flat surface is placed on a sample stage of a fluorescent light observing device, and a fluorescent image is captured and analyzed by the fluorescent light observing device, to identify the coordinates of the fluorescent particles on the flat surface. The fluorescent light observing device may be, for example, a fluorescent microscope or a fluorescent imager.

Specifically, first the fluorescent light observing device identifies, as reference points, the coordinates of at least two points that can be identified by a material analyzing device as well. The points that can be identified by the material analyzing device as well are, for example, points that do not emit fluorescent light, and may be, for example, corners of a rectangular flat surface. Note that points that emit fluorescent light may be identified as reference points, insofar as they can be identified by the material analyzing device as well. The two or more reference points may be, for example, lined up on a straight line.

Figure 2:
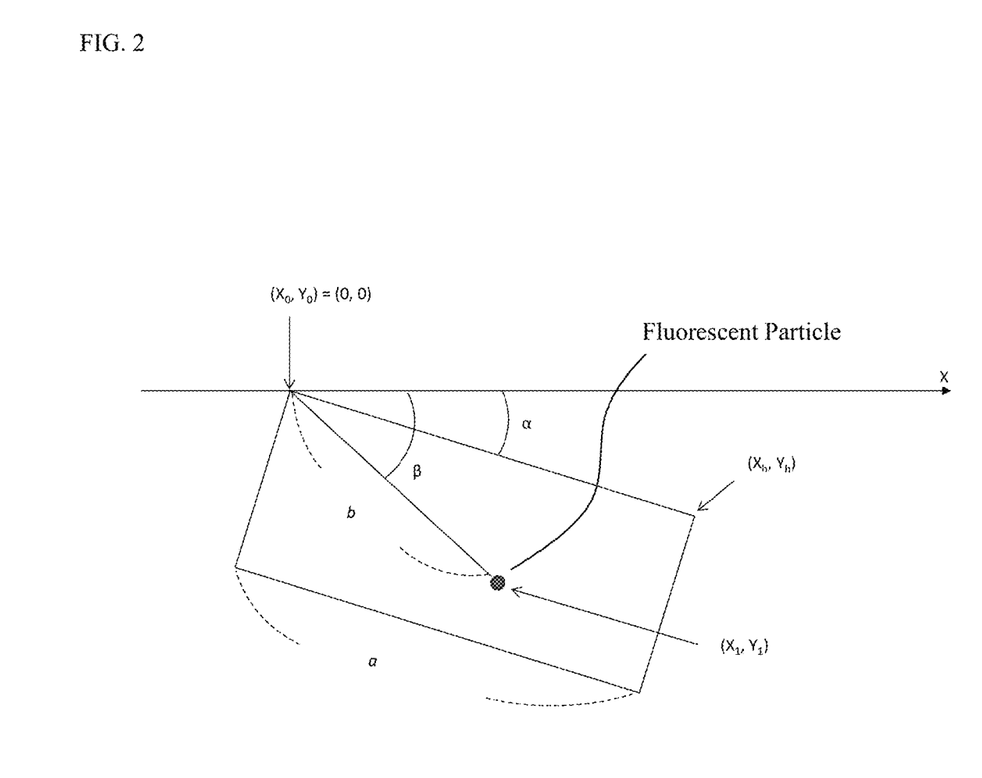
FIG. 2 is a schematic diagram of objects included on a flat surface that is disposed on a sample stage of a fluorescent light observing device according to an example according to the present disclosure.

If, for example, the flat surface has a rectangular shape, the fluorescent light observing device, as illustrated in FIG.

2, identifies, as reference points, the corners on both sides of an edge with a length a. Here the coordinates (X0, Y0) of one of these two reference points (a first reference point) is defined as the origin (0, 0), and the edge that has reference points set on both ends thereof is disposed at an angle α relative to the coordinate axis (the x axis) of the sample stage of the fluorescent light observing device whereon the object that is provided with the flat surface is disposed, the X coordinate of the coordinates (Xh, Yh) of the other reference point (the second reference point) on the sample stage of the fluorescent light observing device is given by Equation (1), below, and the Y coordinate thereof is given by Equation (2), below.

$$Xh = a \cdot \cos \alpha \tag{1}$$

$$Yh = a \cdot \sin \alpha \tag{2}$$

Moreover, the fluorescent light observing device identifies the relative coordinates (X1, Y1) of the fluorescent particle relative to the coordinates (0, 0) of the first reference point. Here when the line with the length b that connects the first reference point and the coordinates (X1, Y1) of a fluorescent particle has an angle β relative to the x axis of the sample stage of the fluorescent light observing device, the X coordinate of the relative coordinates (X1, Y1) of the fluorescent particle, relative to the coordinates (0, 0) of the first reference point, is given by Equation (3), below, and the Y coordinate thereof is given by Equation (4), below.

$$X1 = b \cdot \cos \beta \tag{3}$$

$$Y1 = b \cdot \sin \beta \tag{4}$$

Figure 3:
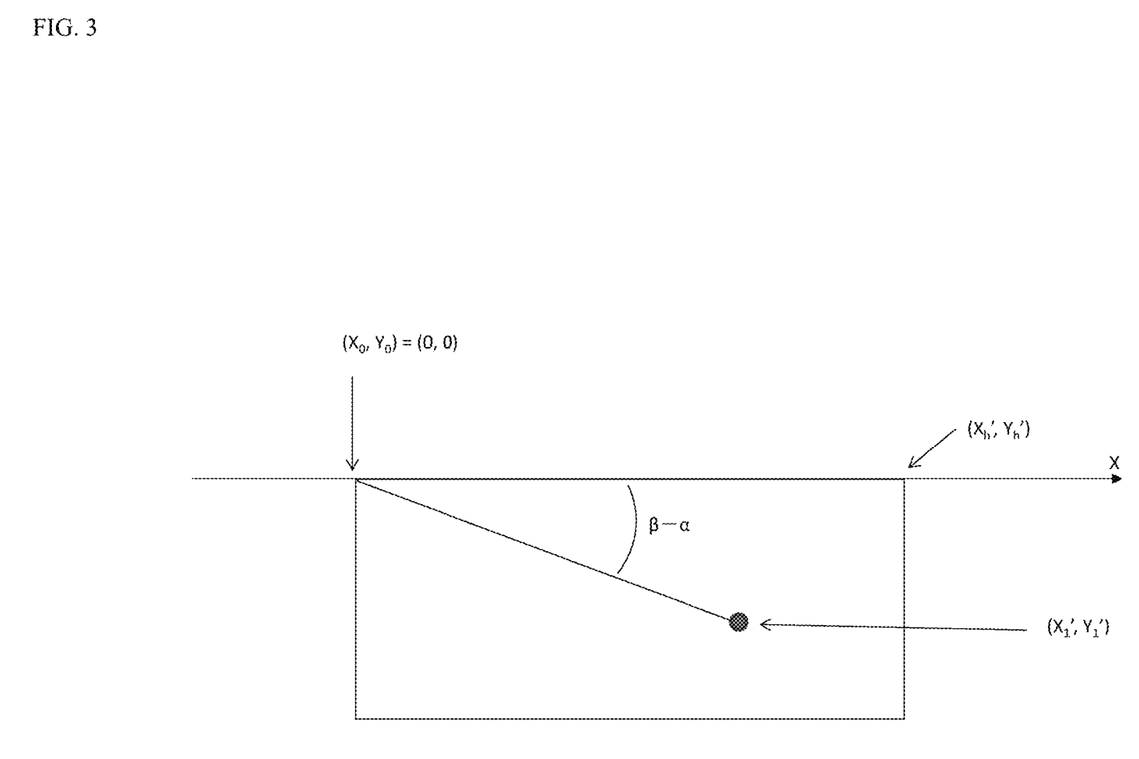
FIG. 3 is a schematic diagram for coordinate conversion of the objects included on the flat surface that is disposed on the sample stage of the florescent light observing device according to the example according to the present disclosure.

Here, as illustrated in FIG. 3, the fluorescent light observing device performs coordinate conversion so as to rotate the rectangle by −α degrees, centered on the first reference point, so that the edge that has the reference points set on both ends thereof will match the x axis of the sample stage of the fluorescent light observing device. The X coordinate of the coordinates (Xh', Yh') of the second reference point that has undergone coordinate conversion is given by Equation (5), below, and the Y coordinate thereof is given by Equation (6), below.

$$Xh' = \{Xh2 + Yh2\}(½) = a \tag{5}$$

$$Yh' = Y0 = 0 \tag{6}$$

Moreover, the X coordinate of the coordinates (X1', Y1') of the fluorescent particle, which have been subjected to coordinate conversion, is given by Equation (7), below, and the Y coordinate thereof is given by Equation (8), below.

$$X1' = b \cdot \cos(\beta - \alpha) \tag{7}$$

$$Y1' = b \cdot \sin(\beta - \alpha) \tag{8}$$

The cosine of the angle α is given by Equation (9), below, and the sine of the angle α is given by Equation (10), below.

$$\cos \alpha = Xh/Xh' = Xh/a \tag{9}$$

$$\sin \alpha = Yh/Xh' = Yh/a \tag{10}$$

From Equations (1) through (4) and Equations (7) through (10), the X coordinate of the relative coordinates (X1', Y1') of the fluorescent particle that has been subjected to coordinate conversion is given by Equation (11), below, and the Y coordinate thereof is given by Equation (12), below. The relative coordinates (X1', Y1') of the fluorescent particle that have been subjected to coordinate conversion express the position of the fluorescent particle relative to the first reference point and the second reference point, which has been subjected to coordinate conversion. In the coordinates (X1', Y1') of the fluorescent particle, which have been subjected to coordinate conversion, the shift in the layout of the object that is included on the flat surface, relative to the coordinate axis of the sample stage of the fluorescent microscope, is corrected.

$$X1' = X1(Xh/Xh') + Y1(Yh/Xh') \tag{11}$$
$$= X1(Xh/a) + Y1(Yh/a)$$

$$Y1' = Y1(Xh/Xh') - X1(Yh/Xh') \tag{12}$$
$$= Y1(Xh/a) - X1(Yh/a)$$

The fluorescent light observing device stores, in a coordinate storing device, the length a of the edge that has the reference points set on both ends thereof, the coordinates (X0, Y0) of the first reference point that has been identified, the coordinates (Xh', Yh') of the second reference point that has been identified and that has been subjected to coordinate conversion, and the relative coordinates (X1', Y1') of the fluorescent particle relative to the first reference point and the second reference point, which have been subjected to coordinate conversion, identified by the fluorescent light observing device.

Note that when a plurality of fluorescent particles have been trapped on the flat surface, the fluorescent light observing device may identify, and store in the coordinate storing device, the respective coordinates for each of the plurality of fluorescent particles.

In Step S103, the object that is equipped with the flat surface that has trapped the fluorescent particle is moved from the sample stage of the fluorescent light observing device to the sample stage of the material analyzing device. The material analyzing device may be a Raman spectroscope, an infrared spectroscope, an electron-beam microanalyzer (EPMA), an energy dispersive x-ray (EDX) analyzer, an auger electron spectrometer (AES), a total reflection fluorescent X-ray analyzer (TXRF), or the like, although there is no limitation thereto. The Raman spectroscope and infrared spectroscope may be provided with microscopes. The EPMA, the EDX device, and the AES device may be provided with scanning electron microscopes (SEM). The Raman spectroscope and infrared spectroscope are adapted to identifying organic materials, and the EPMA, the EDX device, the AES device, and the TXRF device are adapted to identifying inorganic materials, but there are no limitations thereto.

Figure 4:
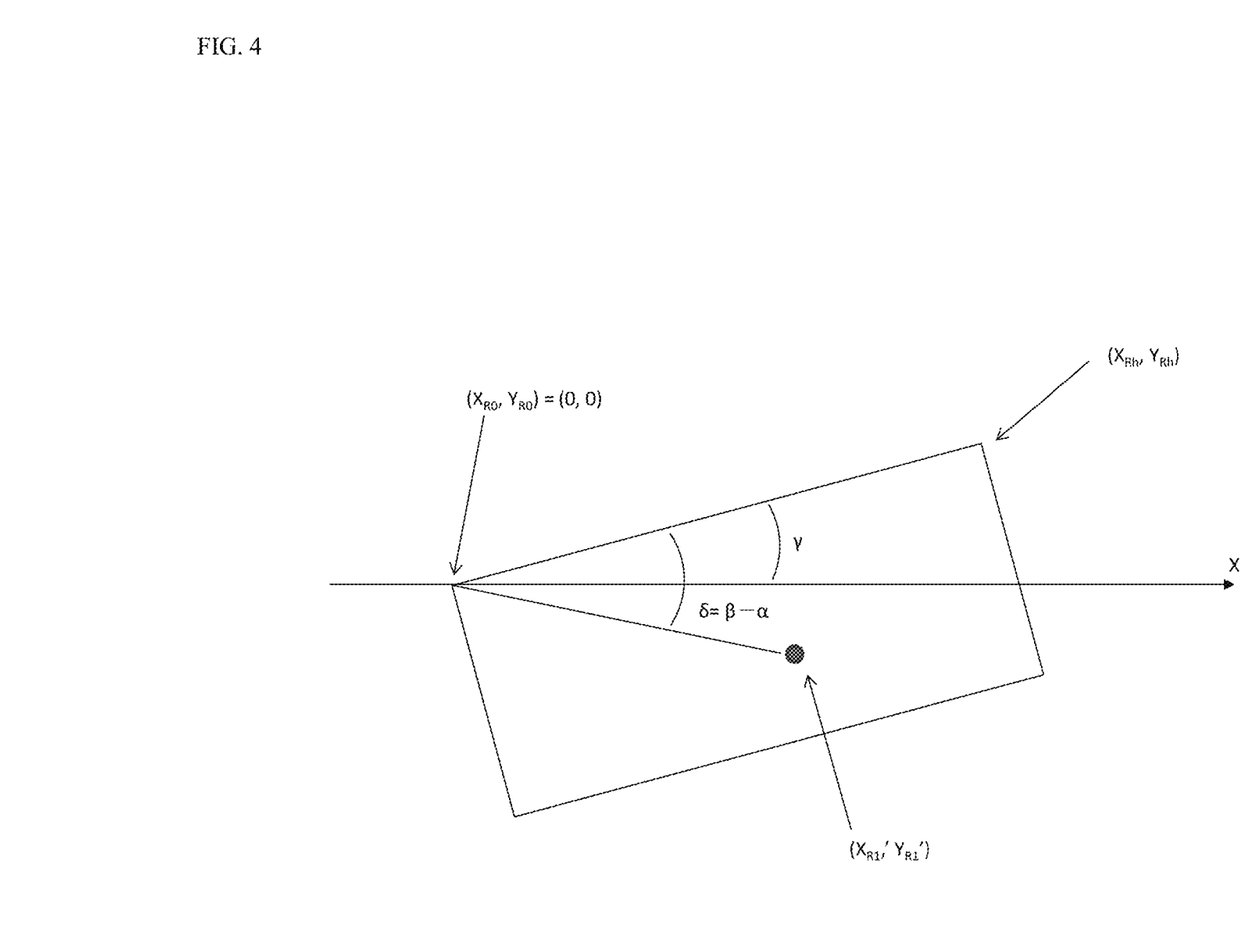
FIG. 4 is a schematic diagram of objects included on a flat surface that is disposed on a sample stage of a material analyzing device according to an example according to the present disclosure.

In Step S104, the material analyzing device identifies the first reference point and the second reference point. Here, as illustrated in FIG. 4, the coordinates (XR0, YR0) of the first reference point is defined as the origin (0, 0), and the edge that has reference points set on both ends thereof is disposed at an angle γ relative to the coordinate axis (the x axis) of the sample stage of the material analyzing device, the X coordinate of the coordinates (XRh, YRh) of the second reference point on the sample stage of the material analyzing device is given by Equation (13), below, and the Y coordinate thereof is given by Equation (14), below.

$$XRh = a \cdot \cos \gamma \tag{13}$$

$$YRh = a \cdot \sin \gamma \tag{14}$$

Moreover, the material analyzing device identifies the relative coordinates (XR1, YR1) of the fluorescent particle relative to the first reference point on the sample stage of the material analyzing device. Here when the angle formed between the edge that has reference points on both ends thereof and the line with the length b that connects the first reference point and the coordinates (X1, Y1) of the fluorescent particle has an angle δ, the X coordinate of the relative coordinates (XR1', YR1') of the fluorescent particle is given by Equation (15), below, and the Y coordinate thereof is given by Equation (16), below.

$$XR1' = b \cdot \cos(\delta - \gamma) \quad (15)$$

$$YR1' = b \cdot \sin(\delta - \gamma) \quad (16)$$

Because the angle δ is given by the difference between the angle β and the angle α (β−α), Equation (15) and Equation (16) mean that the relative coordinates (X1', Y1') of the fluorescent particle relative to the first reference point and the second reference point, identified by the fluorescent light observing device, given by Equation (7) and Equation (8), above, have been further converted based on the angle γ. Equation (15) and Equation (16), given above, become Equation (17) and Equation (18), respectively, given below.

$$\begin{aligned} XR1' &= X1'(XR0 + XRh)/Xh' + Y1'(YRh - YR0)/Xh' \\ &= (X1' \cdot XRh/a) + (Y1' \cdot YRh/a) \end{aligned} \quad (17)$$

$$\begin{aligned} YR1' &= Y1'(XR0 + XRh)/Xh' - X1'(YRh - YR0)/Xh' \\ &= (Y1' \cdot XRh/a) - (X1' \cdot YRh/a) \end{aligned} \quad (18)$$

Here, if the first reference point is actually not at the origin (0, 0) of the sample stage of the material analyzing device, but rather is shifted by a vector (Vx, Vy), the X coordinate of the coordinates (XR1, YR1) of the fluorescent particle in the coordinate system of the sample stage of the material analyzing device is given by Equation (19), below, and the Y coordinate thereof is given by Equation (20), below.

$$XR1 = (X1' \cdot XRh/a) + (Y1' \cdot YRh/a) + Vx \quad (19)$$

$$YR1 = (Y1' \cdot XRh/a) - (X1' \cdot YRh/a) + Vy \quad (20)$$

The material analyzing device reads out, from the coordinate storing device, the value for the length a of the edge having the reference points set on both ends thereof, the value X1' of the X coordinate of the fluorescent particle that has been identified by the fluorescent light observing device and that has been subjected to coordinate conversion, and the value Y1' of the Y coordinate of the fluorescent particle that has been identified by the fluorescent light observing device and that has been subjected to coordinate conversion, and substitutes these values into Equation (19) and Equation (20), described above, to identify the values of the coordinates (XR1, YR1) of the fluorescent particle in the coordinate system of the sample stage of the material analyzing device.

In Step S105 of FIG. 1, the material analyzing device analyzes and identifies the material of the fluorescent particle at the coordinate (XR1', YR1'). If the material analyzing device is, for example, a Raman spectroscope, then the Raman spectroscope measures the Raman scattering spectrum of the fluorescent particle. The Raman spectroscope is provided with a database storing device for storing, for example, a database of Raman scattering spectra for a variety of material. The Raman spectroscope references, in the database, the spectrum that has been obtained, to identify the material of the fluorescent particle that has been measured. The material analyzing device stores, in a material storing device, the material identified for the fluorescent particle. Note that, if necessary, the material analyzing device may move the fluorescent particle into the region that can be analyzed, through moving the sample stage.

Moreover, if the fluorescent light observing device has identified coordinates for a plurality of fluorescent materials, the material analyzing device may identify, and store in the material storing device, the material in each of the plurality of fluorescent materials. Moreover, if the materials are different for each of the plurality of fluorescent materials, the distribution of the types of fluorescent particles may be calculated. Moreover, the type of fluorescent material that is most common may be identified and stored in the material storing device.

Figure 5:
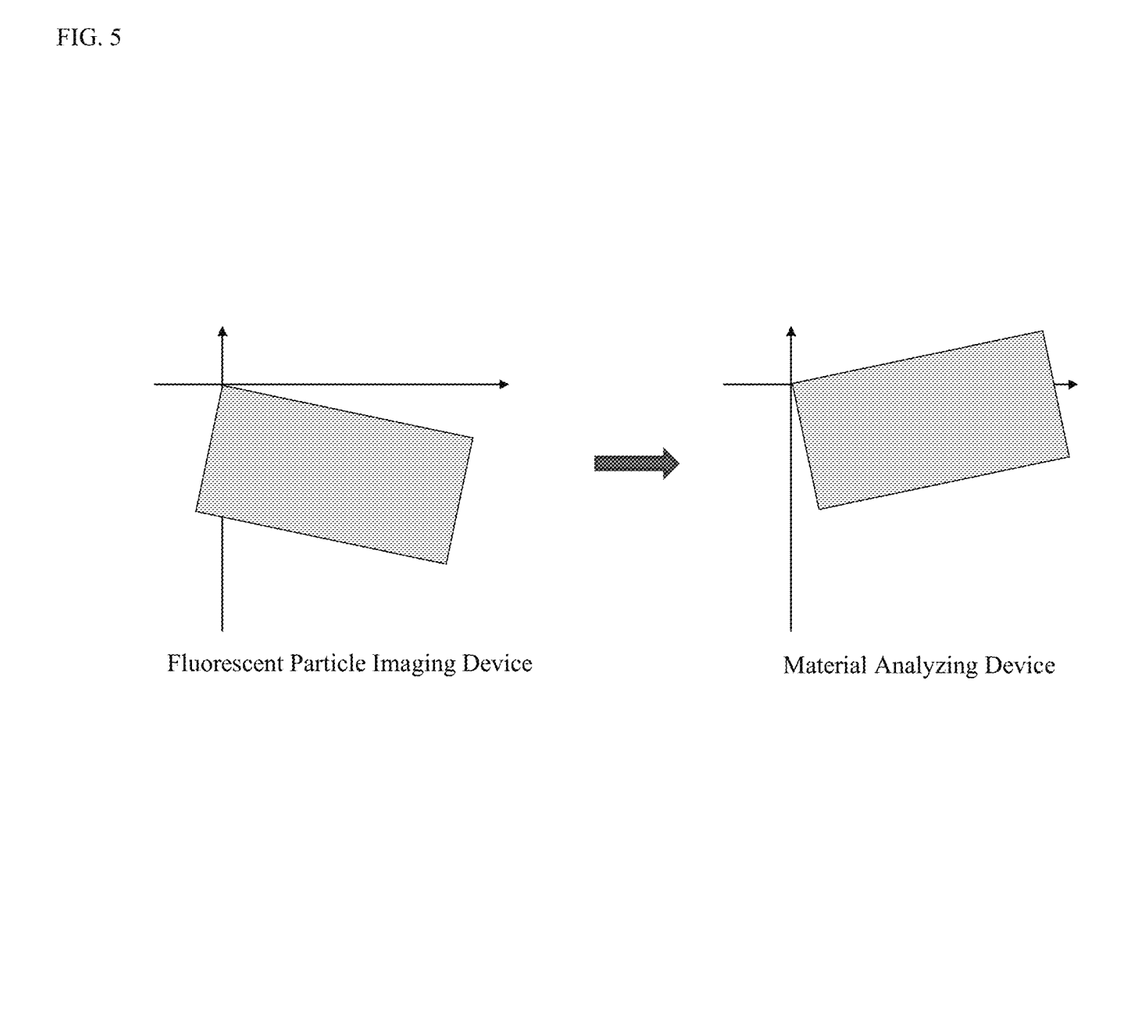
FIG. 5 is a schematic diagram illustrating a shift in the layout of the objects included on the flat surface, according to an example according to the present disclosure.

There may be cases wherein it is difficult to dispose the object that has the flat surface accurately along the coordinate axes of the sample stages of the fluorescent light observing device and material analyzing device. Because of this, in some cases, the locations of the objects that are included on the flat surface may be offsetted between the individual sample stages of the fluorescent light observing device and of the material analyzing device, as illustrated in FIG. 5. Consequently, even if the position of the fluorescent particle is identified by the fluorescent light observing device, the coordinates of the fluorescent particle relative to the coordinate axis may be shifted when the object that includes the flat surface, on which the fluorescent particle has been trapped, is moved from the fluorescent light observing device to the material analyzing device, so that if an analysis were performed, by the material analyzing device, as to the substance at the coordinates identified by the fluorescent light observing device, no fluorescent particle would exist at those coordinates if this shift is not corrected.

In contrast, the fluorescent particle measuring method according to the present example makes it possible to identify accurately the position at which the fluorescent particle exists in the material analyzing device, even if the object that includes the flat surface is moved from the fluorescent light observing device to the material analyzing device, through setting at least two reference points on the object that includes the flat surface and identifying the coordinates of the fluorescent particle relative to these at least two reference points.

In Step S106, an event is identified wherein a fluorescent particle made from the identified material has been produced, based on the material of the fluorescent particle, identified by the material analyzing device. For example, if the material of the fluorescent particles that occurs most often is identified as pollen, then the event that produced the fluorescent particles can be identified as the production of pollen by plants.

Moreover, when the fluid that is to be evaluated is, for example, purified water, if the material of the fluorescent particles is identified as polypropylene, polyethylene, polytetrafluoroethylene (PTFE), olefin, or polycarbonate, polyurethane, or the like, then the event that produced the fluorescent particles can be identified as breakdown of the filter or housing equipped in the purified water manufacturing device. If the material of the fluorescent particle is identified as a silicon rubber, nitrile rubber (NBR), ethylenepropylene rubber (EPDM), fluorine rubber, kalrez, PTFE, or the like, then the event that produced the fluorescent particles can be identified as breakdown of the packing that is provided in the purified water manufacturing device. If the material of the fluorescent particles is identified as Viton, fluorine resin, silicon resin, polyamide, polyphenylene sulfide (PPS), perfluoro, or the like, then the event that produced the fluorescent particles can be identified as breakdown of the pump that is provided in the purified water manufacturing device. If the material of the fluorescent particles is identified as PTFE, or the like, then the event that produced the fluorescent particles can be identified as breakdown of a seal that is provided in the purified water manufacturing device. If the material of the fluorescent particles is identified as a metal material, such as stainless oxide, then the event that produced the fluorescent particles can be identified as breakdown of a pipe that is provided in the purified water manufacturing device.

In Step S107, fluid is drawn into the fluorescent particle measuring device, and the number of fluorescent particles included in the fluid is counted by the fluorescent particle measuring device. The number of fluorescent particles indicates the number, density, and concentration of fluorescent particles. If the fluid is a gas, then the fluorescent particle measuring device, as illustrated in the schematic cross-sectional view in FIG. 6, for example, comprises a case 11 and a first suction device 12 for drawing gas into the case 11 from outside of the fluorescent particle measuring device. The gas that is drawn into the first suction device 12 is emitted from the tip end of a nozzle 13 within the case 11. The gas that is emitted from the tip end of the nozzle 13 is drawn in by a second suction device 14 that is disposed within the case 11 facing the tip end of the nozzle 13.

Figure 6:
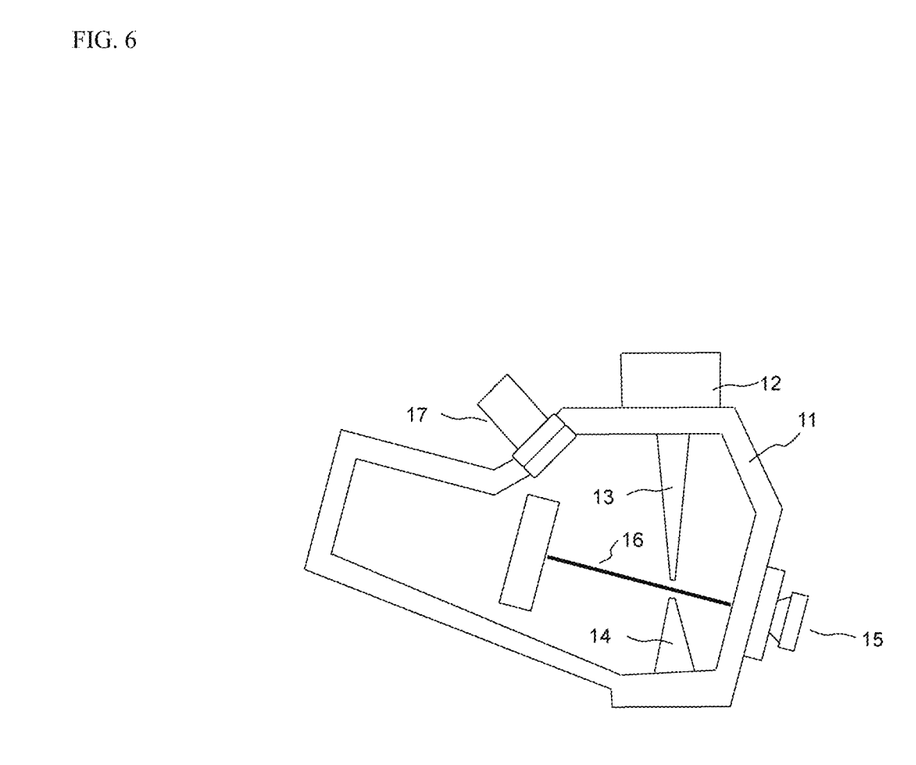
FIG. 6 is a schematic cross-sectional view of a fluorescent particle measuring device according to an example according to the present disclosure.

The fluorescent particle measuring device is further equipped with a light source 15, such as a laser. The light source 15 emits a laser beam 16 toward the gas that is emitted from the tip end of the nozzle 13 and drawn in by the second suction device 14. If particles are included within the gas, then each of the particles that are illuminated by the laser beam 16 will fluoresce. The fluorescent particle measuring device further comprises a fluorescence detector 17. The fluorescence detector 17 detects fluorescent light emitted from the fluorescent particles, and measures the intensities of the fluorescence. Note that if the fluid is a liquid, the liquid may flow through a transparent cell, and the excitation beam may be directed toward the cell.

In Step S108, the material of a fluorescent particle that is measured by the fluorescent particle measuring device is material that is identified by the material analyzing device. If a plurality of types of fluorescent particles is identified by the material analyzing device, the material of the fluorescent particles measured by the fluorescent particle measuring device is defined as the material of the fluorescent particles that are identified most often by the material analyzing device. For example, the fluorescent particle measuring device may read out the fluorescent particle materials identified by the material analyzing device and link numbers of fluorescent particles measured and fluorescent particle materials.

In Step S109, the state of occurrence of an event is monitored by the fluorescent particle measuring device based on the measurement result of the number of fluorescent particles. For example, if there is an increase in the number of fluorescent particles measured wherein the material is found to be pollen, for example, it can be understood that there has been an increase in the occurrence of events wherein pollen is produced by plants, and if there is a decrease in the number of fluorescent particles measured wherein the material is found to be pollen, it can be understood that there has been a reduction and the occurrence of events wherein pollen is produced by plants. This enables real-time monitoring of events correlating to the materials of the fluorescent particles.

Examples

Trapping of Microparticles in a Liquid

Microparticles included in a shock-absorbing fluid were trapped in a membrane by using a filter membrane made of polycarbonate onto which metal has been vapor-deposited (ISOPORE by Merck Millipore, with a pore diameter of 0.45 µm) to filter a commercially available shock-absorbing fluid (STERI-WATER, manufactured by GSI Creos), as a model sample.

(Observation with a Fluorescent Microscope)

Figure 7:
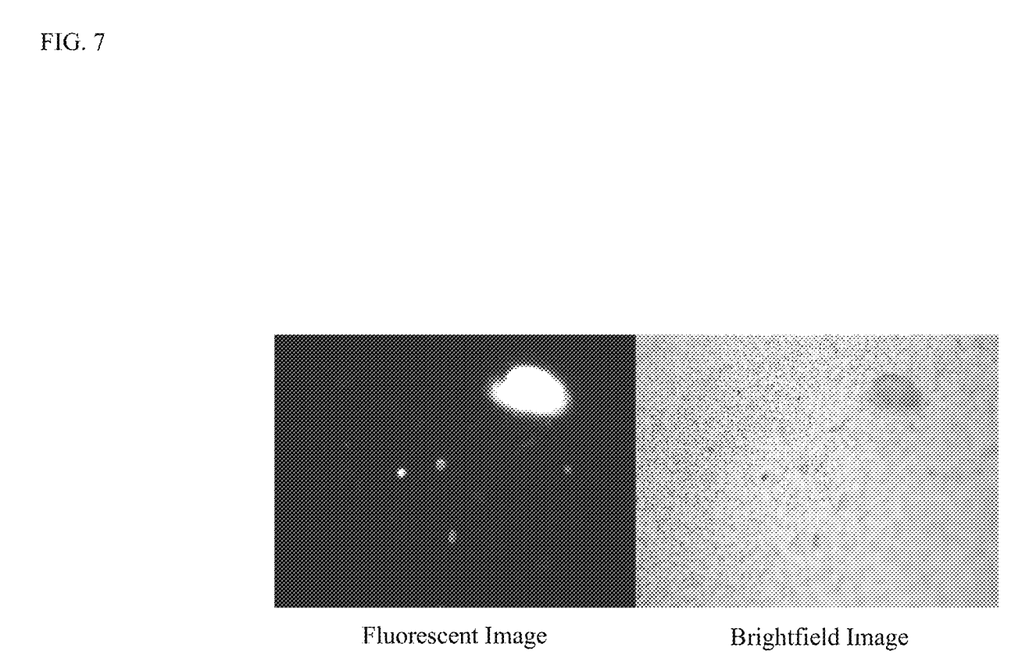
FIG. 7 is a microscopic image according to an example according to the present disclosure.

The membrane, after the filtering has been completed, was applied to a slide glass, and observed under a fluorescent microscope (BX51, manufactured by Olympus) that is provided with a fluorescent mirror unit (U-MNV2, manufactured by Olympus). The fluorescent image obtained through the observation is shown in FIG. 7. Moreover, two coordinates on the membrane were recorded, as reference points, using image processing software (Image-Pro Plus, Media Cybernetics). Given this, particles that exhibit fluorescence were found, and the coordinates of the fluorescent particles were also recorded. Furthermore, the coordinates of the fluorescent particles were converted through Equation (11) and Equation (12), above, and the misalignment of the slide glass relative to the coordinate axis of the sample stage of the fluorescent microscope was corrected.

(Raman Spectral Analysis)

Following this, the slide glass to which the membrane is adhered was placed on the sample stage of a Raman spectroscope (DXR Raman, manufactured by ThermoScientific), to measure the coordinates of the two reference points. Moreover, the coordinates of the reference particles on the sample stage of the Raman spectroscope were identified through calculations in accordance with Equation (15) through (20), based on the coordinates of the two reference points measured on the sample stage of the Raman spectroscope and the coordinates of the fluorescent particles measured on the sample stage of the fluorescent microscope.

The XY stage of the Ramen spectroscope was moved to guide a target fluorescent particle into the field of view based on the coordinates of the fluorescent particle that had been identified. It was also confirmed, based on the positional relationships between the particles within the field of view, that there was a fluorescent particle at the specified coordinates. Thereafter, the Raman scattering of the target fluorescent particle was measured and compared to a database of spectra that had been obtained, to identify the fluorescent particle material.

Figure 8:
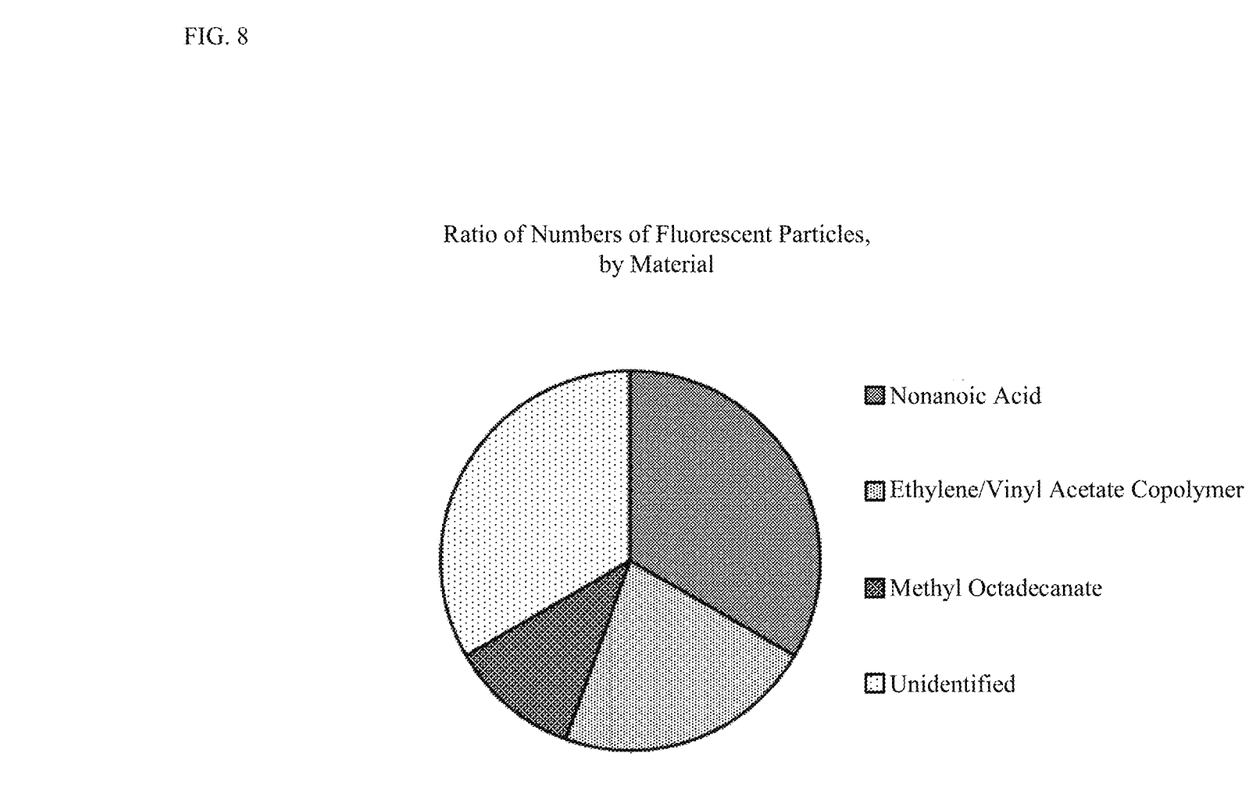
FIG. 8 is a circle graph illustrating ratios of numbers of fluorescent particles for each material according to an example according to the present disclosure.

The result, as illustrated in FIG. 8, was that a fatty acid, such as nonanoic acid or methyl octadecanate, or the like, a fatty acid ester thereof, and a ethylene/vinyl acetate copolymer were identified as the fluorescent particle materials.

(Identification of Events)

Fatty acids and fatty acid ester are used as the resin plasticizing agents and die release agents at the time of molding. From a brightfield microscopic image, liquid droplets and traces wherein the liquid droplets have passed through were seen on the membrane. While the material used for the bottle container filled with the shock-absorbing fluid was polypropylene, in the analysis by the Raman spectroscope there were no fluorescent particles wherein polypropylene was the material.

Note that for the ethylene/vinyl acetate copolymer, this is often used as a membrane material, and thus it is believed that this came from the wrapping material when the membrane was shipped, and thus was not included in the shock-absorbing fluid from the start.

Consequently, the fluorescent particles that exist primarily within the shock-absorbing fluid were identified, in consideration also of the number traces of passage through the membrane, as oil droplets of plasticizing agents or release agents that eluted from the bottle container that contained the shock-absorbing fluid or that were released from the surface of the bottle container.

(Measurements by the Fluorescent Particle Measuring Device)

Figure 9:
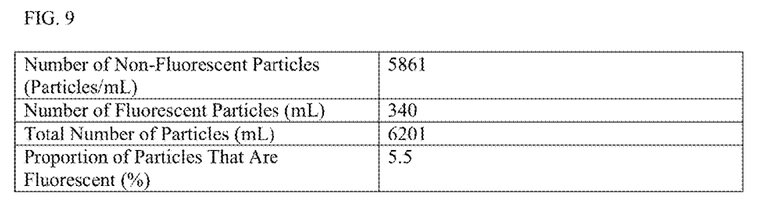
FIG. 9 is a table showing the numbers of particles detected in an example according to the present disclosure.

A fluorescent particle measuring device (IMD-W (registered trademark), manufactured by Azbil BioVigilant) was connected to a pipe wherein a shock-absorbing fluid that is identical to the shock-absorbing fluid that was filtered by the membrane flows, to measure, through the fluorescent particle measuring device, the fluorescent particles included in the shock-absorbing fluid. The result, as illustrated in FIG. 9, was fluorescent light at about 5% of all of the particles that were detected. These fluorescent particles were believed to be made from fatty acids such as nonanoic acid and methyl octadecanate, of fatty acid esters thereof, and of ethylene/vinyl acetate copolymers.

(Monitoring for Events)

The result of continuous measurements, under identical conditions, by the fluorescent particle measuring device was that there were changes in proportions of the fluorescent particles detected by the fluorescent particle measuring device each time the bottle container that holds the shock-absorbing fluid was changed. This made it possible to monitor the changes in the quantities of the oil droplets of the plasticizing agent and the release agent that elute from the bottle container, or that are released from the surface of the bottle container that contains the shock-absorbing fluid.

What is claimed is:

1. A fluorescent particle measuring method, comprising:
   trapping, at a fixed position, a fluorescent particle included in a fluid;
   identifying, by a material analyzing device, a material of the trapped fluorescent particle;
   measuring, by a fluorescent particle measuring device, a number of fluorescent particles included in the fluid; and
   matching the fluorescent particles measured by the fluorescent particle measuring device with the material identified by the material analyzing device.

2. The fluorescent particle measuring method as set forth in claim 1, wherein:
   the trapping step comprises trapping the fluorescent particle on a flat surface;
   the method further including determining the fixed position of the fluorescent particle on the flat surface; and
   the identifying step comprises identifying the material of the fluorescent particle at the determined fixed position.

3. The fluorescent particle measuring method as set forth in claim 2, further comprising:
   determining the fixed position of the fluorescent particle on the flat surface by a fluorescent light observing device.

4. The fluorescent particle measuring method as set forth in claim 3, further comprising:
   identifying, using the fluorescent light observing device, at least two reference points on the flat surface, and
   determining coordinates of a fluorescent particle relative to the at least two reference points.

5. The fluorescent particle measuring method as set forth in claim 4, further comprising:
   identifying, by the material analyzing device, the at least two reference points identified by the fluorescent light observing device, and
   based on an angle formed between a line connecting the at least two reference points and a coordinate axis of a sample stage of the material analyzing device on which is placed an object that is provided with the flat surface, converting the coordinates of the fluorescent particle relative to the at least two reference points to identify coordinates of the fluorescent particle in the coordinate system of the sample stage of the material analyzing device.

6. The fluorescent particle measuring method as set forth in claim 3, wherein the step of determining the position by the fluorescent light observing device comprises:
   identifying at least two reference points on the flat surface,
   identifying coordinates of the fluorescent particle relative to one of the at least two reference points, and
   based on an angle formed between a line connecting the at least two reference points and a coordinate axis of a sample stage of the fluorescent light observing device whereon an object that is provided with the flat surface is placed, converting the coordinates of the fluorescent particle to identify coordinates of the fluorescent particle relative to the at least two reference points.

7. The fluorescent particle measuring method as set forth in claim 3, wherein the fluorescent light observing device is a fluorescent microscope or a fluorescent imager.

8. The fluorescent particle measuring method as set forth in claim 1, wherein the material analyzing device is a Raman spectroscope, an infrared spectroscope, or an electron beam microanalyzer.

9. The fluorescent particle measuring method as set forth in claim 1, further comprising specifying an event in which the fluorescent particle has been produced, based on the identified material of the fluorescent particle.

10. The fluorescent particle measuring method as set forth in claim 9, further comprising monitoring a state of the specified event based on the measured number of fluorescent particles.

11. The fluorescent particle measuring method as set forth in claim 1, wherein the fluid is a gas or a liquid.

12. A fluorescent particle measuring method, comprising:
   trapping a fluorescent particle included in a fluid;
   identifying, by a material analyzing device, a material of the trapped fluorescent particle;
   measuring, by a fluorescent particle measuring device, a number of fluorescent particles included in the fluid;
   matching the fluorescent particles measured by the fluorescent particle measuring device with the material identified by the material analyzing device; and
   specifying an event in which the fluorescent particle has been produced, based on the identified material of the fluorescent particle.

* * * * *